United States Patent
Boyle, Jr.

(10) Patent No.: US 8,246,752 B2
(45) Date of Patent: Aug. 21, 2012

(54) METHODS AND DEVICES TO CLEAR OBSTRUCTIONS FROM MEDICAL TUBES

(75) Inventor: Edward M. Boyle, Jr., Bend, OR (US)

(73) Assignee: Clear Catheter Systems, Inc., Bend, OR (US)

( * ) Notice: Subject to any disclaimer, the term of this patent is extended or adjusted under 35 U.S.C. 154(b) by 562 days.

(21) Appl. No.: 12/425,078

(22) Filed: Apr. 16, 2009

(65) Prior Publication Data

US 2009/0264833 A1    Oct. 22, 2009

Related U.S. Application Data

(63) Continuation-in-part of application No. 12/359,826, filed on Jan. 26, 2009, now Pat. No. 7,951,243.

(60) Provisional application No. 61/189,850, filed on Aug. 22, 2008, provisional application No. 61/023,829, filed on Jan. 25, 2008.

(51) Int. Cl.
  *B08B 9/04*     (2006.01)
  *B08B 1/00*     (2006.01)
  *A61M 1/00*     (2006.01)
  *A61M 5/00*     (2006.01)

(52) U.S. Cl. ............... 134/8; 134/22.11; 134/166 C; 15/104.05; 604/318; 604/319

(58) Field of Classification Search .......... 134/22.12, 134/22.18, 8; 604/541, 319, 322, 506, 128, 604/257, 259, 264; 15/104.16
See application file for complete search history.

(56) References Cited

U.S. PATENT DOCUMENTS

| | | |
|---|---|---|
| 3,416,532 A | 12/1968 | Grossman |
| 3,855,208 A | 12/1974 | Rutner et al. |
| 3,946,741 A | 3/1976 | Adair |
| 3,957,054 A | 5/1976 | McFarlane |
| 3,991,762 A | 11/1976 | Radford |
| 4,006,743 A | 2/1977 | Kowarski |
| 4,056,104 A | 11/1977 | Jaffe |
| 4,148,319 A | 4/1979 | Kasper et al. |

(Continued)

FOREIGN PATENT DOCUMENTS

EP     1 464 335     10/2004

(Continued)

OTHER PUBLICATIONS

Alexoff et al. (1992) "Ion Chromatographic Analysis of High Specific Activity $_{18}$FDG Preparations and Detection of the Chemical Impurity 2-Deoxy-2-chloro-D-Glucose," *Int. J. Rad. Instr. Part. A* 43(11):1313-1322.

(Continued)

*Primary Examiner* — Michael Kornakov
*Assistant Examiner* — Natasha Campbell
(74) *Attorney, Agent, or Firm* — Pearne & Gordon LLP

(57) ABSTRACT

A device for clearing obstructions from a medical tube, such as a chest tube, is disclosed in various embodiments. In embodiments, the device features a guide wire that extends from a drainage canister and can be advanced and withdrawn through a medical tube, such as a chest tube, via an actuator. The guide wire is actuated so as to maintain the sterile field within the chest tube and the associated suction pathway. Methods of clearing a medical tube of obstructions using such a device are also disclosed.

33 Claims, 7 Drawing Sheets

U.S. PATENT DOCUMENTS

| | | |
|---|---|---|
| 4,228,802 A | 10/1980 | Trott |
| 4,257,422 A | 3/1981 | Duncan |
| 4,317,452 A | 3/1982 | Russo et al. |
| 4,324,262 A | 4/1982 | Hall |
| 4,325,961 A | 4/1982 | Kollonitsch et al. |
| 4,358,434 A | 11/1982 | Tzodikov et al. |
| 4,390,517 A | 6/1983 | O'Brien et al. |
| 4,429,693 A | 2/1984 | Blake et al. |
| 4,445,897 A | 5/1984 | Ekbladh et al. |
| 4,465,481 A | 8/1984 | Blake |
| 4,483,870 A | 11/1984 | Kollonitsch et al. |
| 4,523,920 A | 6/1985 | Russo |
| 4,569,344 A | 2/1986 | Palmer |
| 4,638,539 A | 1/1987 | Palmer |
| 4,692,153 A | 9/1987 | Berlin et al. |
| 4,695,588 A | 9/1987 | Kollonitsch et al. |
| 4,696,296 A | 9/1987 | Palmer |
| 4,698,058 A | 10/1987 | Greenfeld et al. |
| 4,706,671 A | 11/1987 | Weinrib |
| 4,723,549 A | 2/1988 | Wholey et al. |
| 4,728,319 A | 3/1988 | Masch |
| 4,743,691 A | 5/1988 | Bey et al. |
| 4,760,091 A | 7/1988 | Carson et al. |
| 4,762,125 A | 8/1988 | Leiman et al. |
| 4,771,772 A | 9/1988 | DeWitt |
| 4,781,678 A | 11/1988 | de Couet et al. |
| 4,865,030 A | 9/1989 | Polyak |
| 4,865,586 A | 9/1989 | Hedberg |
| 4,889,106 A | 12/1989 | Watanabe |
| 4,909,781 A | 3/1990 | Husted |
| 4,921,488 A | 5/1990 | Maitz et al. |
| 4,942,231 A | 7/1990 | Mertens |
| 4,950,232 A | 8/1990 | Ruzicka et al. |
| 4,967,743 A | 11/1990 | Lambert |
| 5,009,659 A | 4/1991 | Hamlin et al. |
| 5,062,835 A | 11/1991 | Maitz et al. |
| 5,073,164 A | 12/1991 | Hollister et al. |
| D328,790 S | 8/1992 | Herweck et al. |
| 5,141,503 A * | 8/1992 | Sewell, Jr. ............... 604/317 |
| 5,188,618 A | 2/1993 | Thomas |
| 5,215,522 A | 6/1993 | Page et al. |
| 5,227,467 A | 7/1993 | Durette et al. |
| 5,240,675 A | 8/1993 | Wilk et al. |
| D340,285 S | 10/1993 | Herweck et al. |
| 5,260,020 A | 11/1993 | Wilk et al. |
| 5,261,877 A | 11/1993 | Fine et al. |
| 5,279,812 A | 1/1994 | Krstenansky et al. |
| 5,297,310 A | 3/1994 | Cox et al. |
| 5,310,912 A | 5/1994 | Neumeyer et al. |
| 5,324,504 A | 6/1994 | Roger, Jr. et al. |
| 5,336,177 A | 8/1994 | Marcus |
| 5,349,950 A | 9/1994 | Ulrich et al. |
| 5,370,610 A | 12/1994 | Reynolds |
| 5,413,779 A | 5/1995 | Kuhar et al. |
| 5,490,503 A | 2/1996 | Hollister |
| 5,505,713 A | 4/1996 | Van Antwerp |
| 5,514,112 A | 5/1996 | Chu et al. |
| 5,520,635 A | 5/1996 | Gelbfish |
| 5,522,801 A | 6/1996 | Wang |
| 5,536,248 A | 7/1996 | Weaver et al. |
| 5,538,511 A | 7/1996 | Van Antwerp |
| 5,599,299 A | 2/1997 | Weaver et al. |
| 5,599,300 A | 2/1997 | Weaver et al. |
| 5,630,823 A | 5/1997 | Schmitz-Rode et al. |
| 5,637,759 A | 6/1997 | Hearst et al. |
| 5,653,696 A | 8/1997 | Shiber |
| 5,688,234 A | 11/1997 | Frisbie |
| 5,693,011 A | 12/1997 | Onik |
| 5,698,179 A | 12/1997 | Neumeyer et al. |
| 5,715,815 A | 2/1998 | Lorenzen et al. |
| 5,768,741 A | 6/1998 | Leiman |
| 5,772,261 A | 6/1998 | Magram |
| 5,773,614 A | 6/1998 | Godfrey et al. |
| 5,788,678 A | 8/1998 | Van Antwerp |
| 5,788,681 A | 8/1998 | Bates et al. |
| 5,788,710 A | 8/1998 | Bates et al. |
| 5,807,330 A | 9/1998 | Teitelbaum |
| 5,808,146 A | 9/1998 | Goodman et al. |
| 5,830,127 A | 11/1998 | DeCastro |
| 5,843,028 A | 12/1998 | Weaver et al. |
| 5,853,696 A | 12/1998 | Elmaleh et al. |
| 5,868,720 A | 2/1999 | Van Antwerp |
| 5,895,398 A | 4/1999 | Wensel et al. |
| 5,897,534 A | 4/1999 | Heim et al. |
| 5,902,314 A | 5/1999 | Koch |
| 5,911,710 A | 6/1999 | Barry et al. |
| 5,911,734 A | 6/1999 | Tsugita et al. |
| 5,913,852 A | 6/1999 | Magram |
| 5,921,952 A | 7/1999 | Desmond, III et al. |
| 5,928,218 A | 7/1999 | Gelbfish |
| 5,931,821 A | 8/1999 | Weilbacher et al. |
| 5,957,932 A | 9/1999 | Bates et al. |
| 5,964,223 A | 10/1999 | Baran |
| 5,989,241 A | 11/1999 | Plishka et al. |
| 6,045,623 A | 4/2000 | Cannon |
| 6,080,170 A | 6/2000 | Nash et al. |
| 6,082,361 A | 7/2000 | Morejon |
| 6,096,874 A | 8/2000 | Wallace et al. |
| 6,129,697 A | 10/2000 | Drasler et al. |
| 6,168,603 B1 | 1/2001 | Leslie et al. |
| 6,183,450 B1 | 2/2001 | Lois |
| 6,245,326 B1 | 6/2001 | Topping et al. |
| 6,248,100 B1 | 6/2001 | de Toledo et al. |
| 6,264,624 B1 | 7/2001 | Desmond, III et al. |
| 6,299,604 B1 | 10/2001 | Ragheb et al. |
| 6,344,179 B1 | 2/2002 | Goodman |
| 6,383,196 B1 | 5/2002 | Leslie et al. |
| 6,399,042 B1 | 6/2002 | Goodman |
| 6,436,112 B2 | 8/2002 | Wensel et al. |
| 6,454,775 B1 | 9/2002 | Demarais et al. |
| 6,485,497 B2 | 11/2002 | Wensel et al. |
| 6,508,789 B1 | 1/2003 | Sinnott et al. |
| 6,514,273 B1 | 2/2003 | Voss et al. |
| 6,530,935 B2 | 3/2003 | Wensel et al. |
| 6,547,761 B2 | 4/2003 | Liu |
| 6,562,024 B2 | 5/2003 | Alvarez de Toledo et al. |
| 6,582,400 B1 | 6/2003 | Hawk et al. |
| 6,629,956 B1 | 10/2003 | Polidoro et al. |
| 6,638,253 B2 | 10/2003 | Breznock |
| 6,660,014 B2 | 12/2003 | Demarais et al. |
| 6,663,650 B2 | 12/2003 | Sepetka et al. |
| 6,679,262 B1 | 1/2004 | Morejon |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,699,331 B1 | 3/2004 | Kritzler |
| 6,702,830 B1 | 3/2004 | Demarais et al. |
| 6,730,104 B1 | 5/2004 | Sepetka et al. |
| 6,740,096 B2 | 5/2004 | Teague et al. |
| 6,767,338 B2 | 7/2004 | Hawk et al. |
| 6,780,193 B2 | 8/2004 | Leslie et al. |
| 6,783,536 B2 | 8/2004 | Vilsmeier et al. |
| 6,824,545 B2 | 11/2004 | Sepetka et al. |
| 6,849,061 B2 | 2/2005 | Wagner |
| 6,866,657 B2 | 3/2005 | Shchervinsky |
| 6,893,418 B2 | 5/2005 | Liu |
| 6,893,424 B2 | 5/2005 | Shchervinsky |
| 6,902,550 B2 | 6/2005 | Want et al. |
| 6,905,484 B2 | 6/2005 | Buckman et al. |
| 6,945,977 B2 | 9/2005 | Demarais et al. |
| 7,004,954 B1 | 2/2006 | Voss et al. |
| 7,028,707 B2 | 4/2006 | Corbeil et al. |
| 7,101,380 B2 | 9/2006 | Khachin et al. |
| 7,125,402 B1 | 10/2006 | Yarger |
| 7,135,010 B2 | 11/2006 | Buckman et al. |
| 7,141,038 B2 | 11/2006 | Whalen et al. |
| 7,211,067 B2 | 5/2007 | Hawk et al |
| 7,229,433 B2 | 6/2007 | Mullen |
| 7,241,287 B2 | 7/2007 | Shehada et al. |
| 7,241,299 B2 | 7/2007 | Gerard |
| 7,244,251 B2 | 7/2007 | Shehada et al. |
| 7,252,659 B2 | 8/2007 | Shehada et al. |
| 7,264,616 B2 | 9/2007 | Shehada et al. |
| 7,267,671 B2 | 9/2007 | Shehada |
| 7,285,126 B2 | 10/2007 | Sepetka et al. |
| 7,326,197 B2 | 2/2008 | Breznock et al. |
| 7,338,478 B2 | 3/2008 | Leiboff |

| | | |
|---|---|---|
| 7,338,501 B2 | 3/2008 | Teague et al. |
| 7,419,483 B2 | 9/2008 | Shehada |
| 7,610,106 B2 | 10/2009 | Yacoubian |
| 7,686,801 B2 | 3/2010 | Corbeil et al. |
| 7,780,639 B2 | 8/2010 | Van Lue |
| 7,799,046 B2 | 9/2010 | White et al. |
| 7,811,293 B2 | 10/2010 | Simpson et al. |
| 7,867,241 B2 | 1/2011 | Brock et al. |
| 7,992,561 B2 | 8/2011 | Baker, Jr. et al. |
| 2001/0018572 A1 | 8/2001 | Kinsey et al. |
| 2002/0058915 A1 | 5/2002 | Wakabayashi |
| 2002/0099184 A1 | 7/2002 | Goodman |
| 2002/0128601 A1 | 9/2002 | Reilly et al. |
| 2003/0069551 A1 | 4/2003 | Bradley, III et al. |
| 2003/0216760 A1 | 11/2003 | Welch |
| 2004/0006331 A1 | 1/2004 | Shchervinsky |
| 2004/0073243 A1 | 4/2004 | Sepetka et al. |
| 2004/0078026 A1 | 4/2004 | Wagner |
| 2004/0092956 A1 | 5/2004 | Liddicoat et al. |
| 2004/0181191 A1 | 9/2004 | Teitelbaum |
| 2004/0219028 A1 | 11/2004 | Demarais et al. |
| 2004/0230132 A1 | 11/2004 | Shehada |
| 2005/0033348 A1 | 2/2005 | Sepetka et al. |
| 2005/0055033 A1 | 3/2005 | Leslie et al. |
| 2005/0059995 A1 | 3/2005 | Sepetka et al. |
| 2005/0085545 A1 | 4/2005 | Susacca et al. |
| 2005/0085849 A1 | 4/2005 | Sepetka et al. |
| 2005/0125024 A1 | 6/2005 | Sepetka et al. |
| 2005/0154373 A1 | 7/2005 | Deutsch |
| 2005/0159790 A1 | 7/2005 | Shalev |
| 2005/0171478 A1 | 8/2005 | Selmon et al. |
| 2005/0171566 A1 | 8/2005 | Kanamaru |
| 2005/0192458 A1 | 9/2005 | Goodman et al. |
| 2005/0197350 A1 | 9/2005 | Sekiguchi et al. |
| 2005/0216030 A1 | 9/2005 | Sepetka et al. |
| 2005/0216050 A1 | 9/2005 | Sepetka et al. |
| 2005/0226776 A1 | 10/2005 | Brady et al. |
| 2005/0228363 A1 | 10/2005 | Leiboff |
| 2005/0228417 A1 | 10/2005 | Teitelbaum et al. |
| 2005/0288686 A1 | 12/2005 | Sepetka et al. |
| 2006/0004404 A1 | 1/2006 | Khachin et al. |
| 2006/0142697 A1 | 6/2006 | Hawk et al. |
| 2006/0167416 A1 | 7/2006 | Mathis et al. |
| 2006/0195069 A1 | 8/2006 | Opie et al. |
| 2006/0195137 A1 | 8/2006 | Sepetka et al. |
| 2006/0206097 A1 | 9/2006 | Breznock et al. |
| 2006/0264974 A1 | 11/2006 | Khachin et al. |
| 2006/0264988 A1 | 11/2006 | Boyle |
| 2006/0292073 A1 | 12/2006 | Goodman et al. |
| 2007/0032779 A1 | 2/2007 | Accisano et al. |
| 2007/0049904 A1 | 3/2007 | Deutsch |
| 2007/0078389 A1 | 4/2007 | Whalen et al. |
| 2007/0082879 A1 | 4/2007 | Goodman et al. |
| 2007/0083189 A1 | 4/2007 | Lampropoulos et al. |
| 2007/0135795 A1 | 6/2007 | De Paulis et al. |
| 2007/0149946 A1 | 6/2007 | Viswanathan et al. |
| 2007/0179513 A1 | 8/2007 | Deutsch |
| 2007/0198030 A1 | 8/2007 | Martin et al. |
| 2007/0208371 A1 | 9/2007 | French et al. |
| 2007/0288036 A1 | 12/2007 | Seshadri et al. |
| 2008/0045881 A1 | 2/2008 | Teitelbaum et al. |
| 2008/0051720 A1 | 2/2008 | Nash et al. |
| 2008/0091146 A1 | 4/2008 | Solovay et al. |
| 2008/0109032 A1 | 5/2008 | Sepetka et al. |
| 2008/0119869 A1 | 5/2008 | Teague et al. |
| 2008/0177276 A1 | 7/2008 | Teague et al. |
| 2008/0177296 A1 | 7/2008 | Sepetka et al. |
| 2008/0183197 A1 | 7/2008 | Sepetka et al. |
| 2008/0183198 A1 | 7/2008 | Sepetka |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0215077 A1 | 9/2008 | Sepetka et al. |
| 2008/0234706 A1 | 9/2008 | Sepetka et al. |
| 2009/0062772 A1 | 3/2009 | Wakeford et al. |
| 2009/0326513 A1 | 12/2009 | Deutsch et al. |

FOREIGN PATENT DOCUMENTS

| | | |
|---|---|---|
| WO | 94/03226 A1 | 2/1994 |
| WO | WO 97/17092 | 5/1997 |
| WO | WO 97/43285 | 11/1997 |
| WO | WO 99/01149 | 1/1999 |
| WO | WO 02/00209 | 1/2002 |
| WO | WO 03/078358 | 9/2003 |
| WO | WO 03/093412 | 11/2003 |
| WO | WO 2004/056725 | 7/2004 |
| WO | WO 2004098654 A2 * | 11/2004 |
| WO | 2004108051 | 12/2004 |
| WO | WO 20005/021485 | 3/2005 |
| WO | WO 2005/030025 | 4/2005 |
| WO | WO 2005/030677 | 4/2005 |
| WO | WO 2005/051384 | 6/2005 |
| WO | 2005067647 | 7/2005 |
| WO | WO 2005/061110 | 7/2005 |
| WO | 2006071855 | 7/2006 |
| WO | 2006074283 | 7/2006 |
| WO | 2007090057 | 8/2007 |
| WO | 2007098376 | 8/2007 |

OTHER PUBLICATIONS

Berge et al. (1977) "Pharmaceutical Salts," *J. Pharm. Sci.* 66:1-19.
Bergmann et al. (1962) "Organic Fluorine Compounds Part XXVII. Fluorinated α-Aminoisobutyric Acids," *J. Chem. Soc.* :3462-3463.
Betz et al. (1978) "Polarity of the Blood-Brain Barrier: Neutral Amino Acid Transport into Isolated Brain Capillaries," *Science* 202:225-227.
Bey et al. (1979) "Direct Synthesis of Alpha-Halogenomethyl-Alpha-Amino Acids from the Parent Alpha-Amino Acids," *J. Org. Chem.* 44:15:2732-2742.
Blough et al. (1996) "Synthesis and Transporter Binding Properties of 3β-(4'-Alkyl-, 4'Alkenyl-, and 4'A;kenyl-, and 4'Alkynylphenyl)nortropane-2β-Carboxylic Acid Methyl Esters: Serotonin Transporter Selective Analogs," *J. Med. Chem.* 39(20):4027-4035.
Blough et al. (1997) "3β-(4-Ethyl-3-iodophenyl)nortropane-2β-carboxylic Acid Methyl Ester as a High-Affinity Selective Ligand for the Serotonin Transporter" *J. Med. Chem.* 40(24):3861-3864.
Bodsch et al. (1988) "Biochemical and Autoradiographic Study of Cerebral Protein Synthesis with Fluorine-18 Fluorophenylalanine and Carbon-14 Fluorophenylalanine," *J. Neurochem.* 50(3):979-983.
International Search Report and Written Opinion issued Jan. 13, 2010 in corresponding PCT Application PCT/US2009/045954.
International Search Report and Written Opinion issued Dec. 16, 2009 in related PCT Application PCT/US2009/032000.
Prosecution History of U.S. Appl. No. 10/415,843.
Prosecution History of U.S. Appl. No. 10/555,130.
Prosecution History of U.S. Appl. No. 12/359,826.
International Search Report and International Preliminary Search Report on Patentability from PCT Application Serial No. PCT/US01/45648, Dated Sep. 1, 2004.
International Search Report and Written Opinion from PCT Application Serial No. PCT/US04/13728, Dated Nov. 2, 2005.
European Search Report from European Patent Application 01986082.4, Dated Apr. 11, 2006.

* cited by examiner

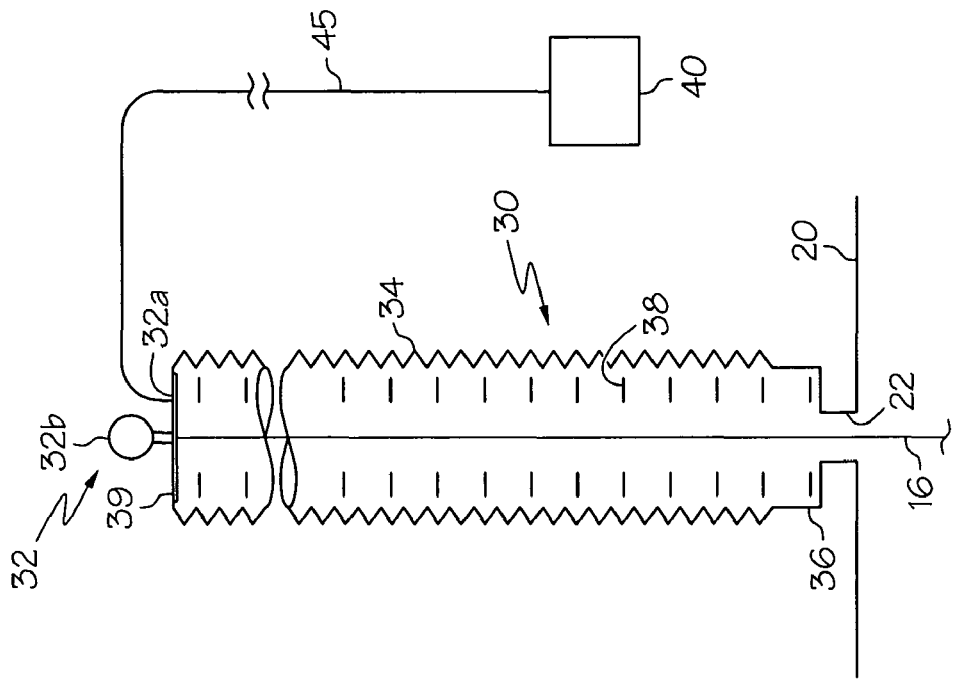
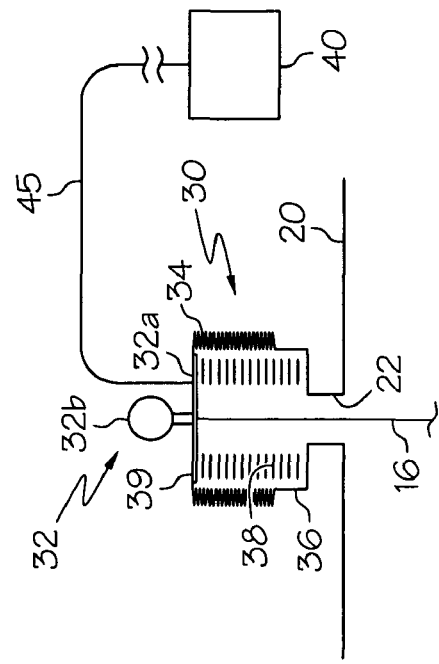
FIG. 2B
FIG. 2A

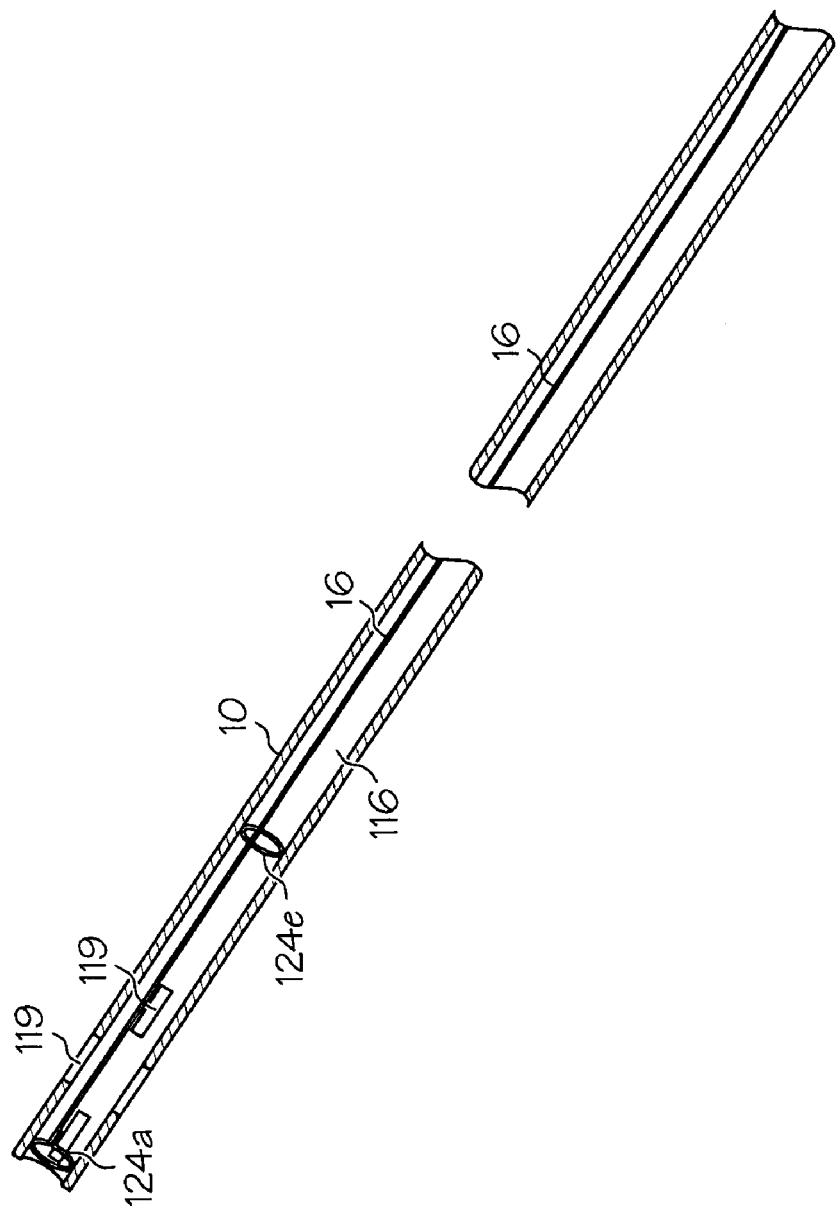

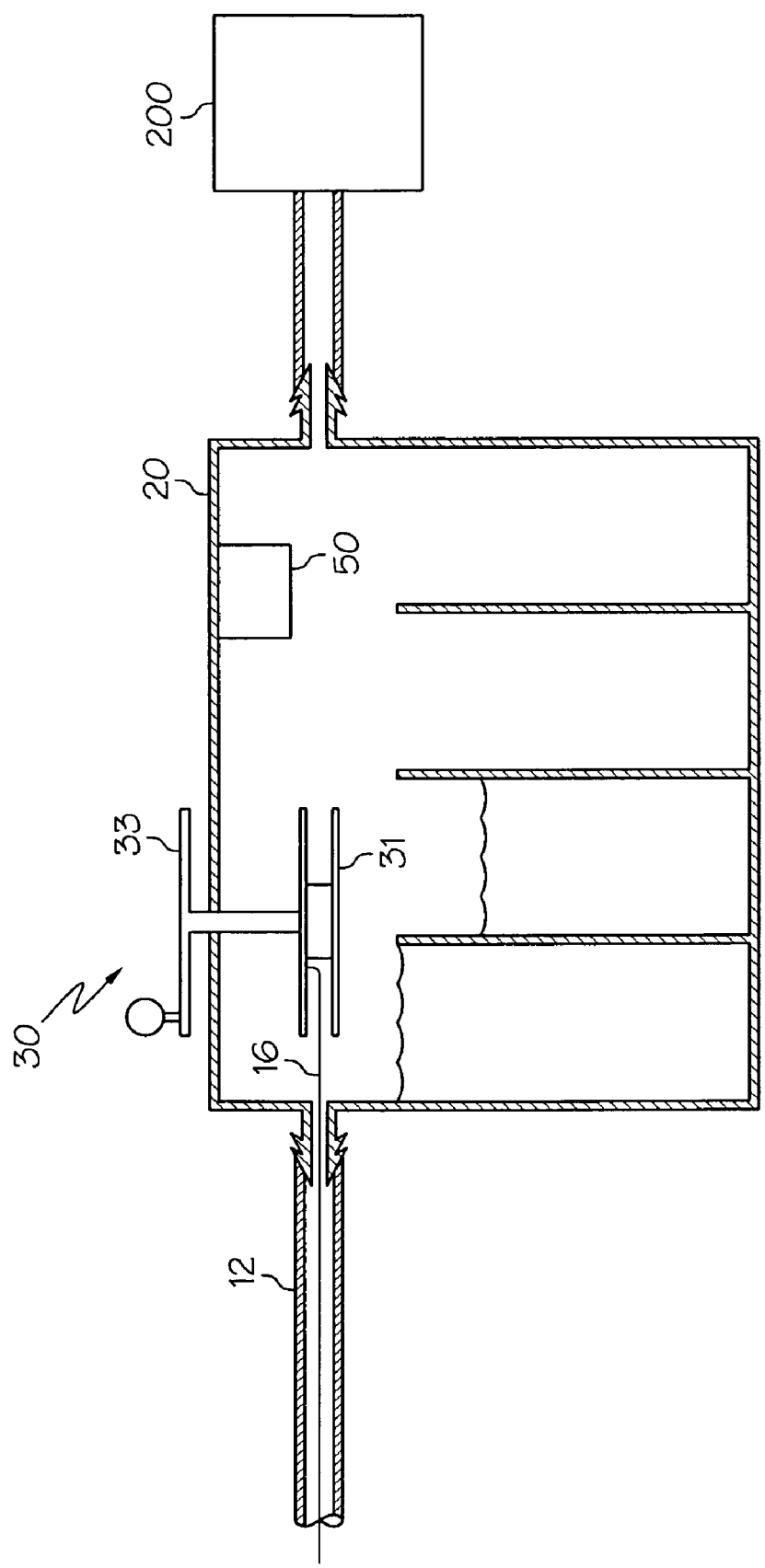

METHODS AND DEVICES TO CLEAR OBSTRUCTIONS FROM MEDICAL TUBES

CROSS-REFERENCE TO RELATED APPLICATIONS

This application is a continuation-in-part of U.S. patent application Ser. No. 12/359,826 filed Jan. 26, 2009, which claims the benefit of U.S. provisional patent application Ser. No. 61/189,850 filed Aug. 22, 2008, and U.S. provisional patent application Ser. No. 61/023,829 filed Jan. 25, 2008. The contents of all the foregoing applications are incorporated herein by reference.

BACKGROUND

1. Field of the Invention

The invention relates to methods and devices to clear obstructive debris from medical tubes. More particularly, it relates to such a device having a clearance member that can be actuated to draw such debris proximally in a medical tube without compromising the sterile field.

2. Description of Related Art

Millions of medical tubes are used every year to drain bodily fluids and secretions from within body orifices. For example, such tubes can be used to drain fluid from one's bladder, from the colon or other portions of the alimentary tract, or from the lungs or other organs in conjunction with various therapies. Medical tubes also are used to drain blood and other fluids that typically accumulate within the body cavity following traumatic surgery. In all these cases, a tube is inserted into the patient so that its terminal end is provided in or adjacent the space where it is desired to remove accumulated or pooled fluid, and the proximal end remains outside the patient's body, where it is typically connected to a suction source.

One of the biggest categories of patients requiring medical tube drainage is patients who have had heart and lung surgery, nearly all of whom require at least one chest tube to drain the space around the heart and lungs after surgery. Chest tubes are long, usually semi-stiff, plastic tubes that are inserted into the chest in the vicinity of the heart and lungs to drain collections of fluids or air from within the pleura, the mediastinum or pericardial space, or from within the thoracic cavity generally.

In all cases, fluid and other material accumulating in the vicinity of the medical tube's distal end (within the patient) is drawn through that tube and out of the space where it accumulated via suction applied at the tube's proximal end. Ideally, the medical tube will remain free from clots and other debris that may partially or totally obstruct the suction pathway within the medical tube. Unfortunately, however, bodily secretions (particularly those including blood or blood platelets) often form clots within medical tubes, which can partially or totally obstruct the suction pathway within the tube.

Obstruction of a medical tube can impact its effectiveness to remove the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax. In addition to chest tubes used in heart, lung and trauma surgery, other medical tubes are prone to clogging as well, including feeding tubes, surgical wound drains, urinary catheters, cardiovascular catheters and others.

There are few effective techniques to manage medical tube clogging when it occurs. During the perioperative period following chest surgery or trauma, clinicians will undertake measures to try to remove any debris (such as a clot) that has accumulated or formed within the chest tube, to keep the tube clear. One method is to simply tap the tube to try and break up the debris. Another method is referred to as 'milking the tube.' 'Milking' involves using one's fingers, or a rudimentary device composed of a pair of pliers with rollers fashioned onto its jaws, to compress the tube over the debris to try and break it up. The goal is to loosen the debris, or to break it into smaller pieces, so it can be more readily drawn out of the tube via suction applied at the proximal end.

Another technique is fan folding. In this technique, the clinician bends the chest tube in various ways to try to break up any long clots or other obstructions that extend along the axis of the medical tube. The aim is to produce several smaller pieces of debris, as opposed to one long piece, that will be more readily drawn proximally via the suction applied at the tube's proximal end. Still another technique is known as 'stripping.' Here, the clinician takes two fingers lubricated in some fashion, or the improvised device composed of a pair of pliers with rollers mentioned above, and 'strips' the tube. This is achieved by compressing the tube initially near where it enters the patient, and drawing the compressing apparatus (one's fingers or other compression device) proximally, with compression still applied, along the tube's length toward the suction source. This is done repeatedly to try and work any obstructive debris out from the tube and toward the suction source.

None of the above techniques is particularly effective. Moreover, they are time consuming and can be quite painful if the patient is awake and alert when they are performed, due to tugging on the medical tube. Tugging on chest tubes whose terminal ends have been placed near the pleura or pericardium can be especially painful. In addition, the 'stripping' technique is known to generate short bursts of extreme negative pressure within chest tubes, which in turn draws a strong suction in the body cavity where its terminal end has been placed. This can be quite dangerous in certain circumstances. For example, negative pressures of magnitude greater than −300 cm of water can be generated adjacent suture lines on coronary anastomosis, etc., which can disrupt some of the work that was done during a prior surgery. As a result, many surgeons have banned stripping their patients' chest tubes due to the potential for complications.

When the above techniques fail to clear a potentially dangerous clot within the tube, a more invasive technique must be used. This requires establishment of a sterile field around the chest tube, which is disconnected from the suction source to manually insert a suction catheter to clear the debris. This is known as open chest tube suctioning, and it can be effective to clear a clogged chest tube. But it is highly undesirable for a number of reasons. First, it compromises the sterile field within the chest tube system by exposing the internal environment within that system to the external environment, potentially introducing bacteria inside the chest. Second, the closed system (suction source to chest tube to body space within the chest) typically must be breached to insert the catheter inside the chest tube. Breaking the seal on this system causes loss of the normal physiologic negative pressure inside the chest. This can result in lung collapse (pneumothorax) while suctioning the chest tube. Additionally, the suction catheter can easily be passed beyond the end of the chest tube, which has the potential to injure the heart or lungs, which could be life threatening. Finally, this procedure is time consuming and usually can only be performed by physicians due to the associated dangers. Thus it is only occasionally done in extreme situations when a clogged chest tube is causing a serious acute problem.

Currently, surgeons often implant two or more medical tubes, or employ large-diameter tubes, following surgery to provide additional drainage capacity and avoid potentially life-threatening complications of a clogged tube. Methods and apparatus are desirable to keep medical tubes from clogging or to clear them reliably without having to breach the closed system between the suction source and the body cavity requiring drainage. Such methods/apparatus may allow surgeons to place fewer tubes post-surgery, or to select tubes having smaller diameters, both of which will reduce patient discomfort and recovery time. Placement of fewer tubes also will minimize the risk of infection.

SUMMARY OF THE INVENTION

A device for clearing obstructions from a medical tube is provided. The device includes a drainage canister having a drainage port for the introduction of material into the canister, and a guide-member actuator. A guide member extends through the drainage port. The guide-member actuator is operable to advance or withdraw the guide member through the drainage port.

A method of clearing obstructions from a medical tube is also provided, including the steps of establishing fluid communication between the medical tube and an interior of a drainage canister for collecting material drained through the medical tube, and advancing a guide member that extends from the canister through the medical tube.

A medical tube drainage system is provided. A drainage canister has a fluid chamber. A drainage tube has a proximal end and a distal end, wherein the proximal end is coupled to the drainage canister. The drainage tube has a lumen therethrough, and is in fluid communication with the fluid chamber. A medical tube has a proximal end and a distal end, and a lumen therethrough. The proximal end of the medical tube is coupled to the distal end of the drainage tube. The medical-tube lumen is in fluid communication with the lumen of the drainage tube. A guide wire has a proximal portion terminating at a proximate end and a distal portion terminating at a distal end. The proximal end of the guide wire extends from the drainage canister. The proximal portion of the guide wire extends through the fluid chamber, and the distal portion of the guide wire extends through the lumen of the drainage tube and into the lumen of the medical tube, wherein the guide wire is adapted such that the distal end can be extended into and withdrawn from the medical tube by pushing and pulling the guide wire's proximal end. The distal end of the guide wire is adapted to dislodge obstructing material from the medical tube.

BRIEF DESCRIPTION OF THE DRAWINGS

FIGS. 2a and 2b are close-up cross-sectional views of an embodiment of a guide-member actuator, shown in different stages of actuation corresponding respectively to the illustrations in FIGS. 1a and 1b.

FIG. 4 is a perspective view, partially in section, of a guide member inserted in a chest tube, according to an embodiment hereafter described.

FIG. 7 is a schematic side view, in section, illustrating an embodiment of a guide-member actuator as hereafter described.

DETAILED DESCRIPTION OF PREFERRED EMBODIMENTS

Figure 1A:
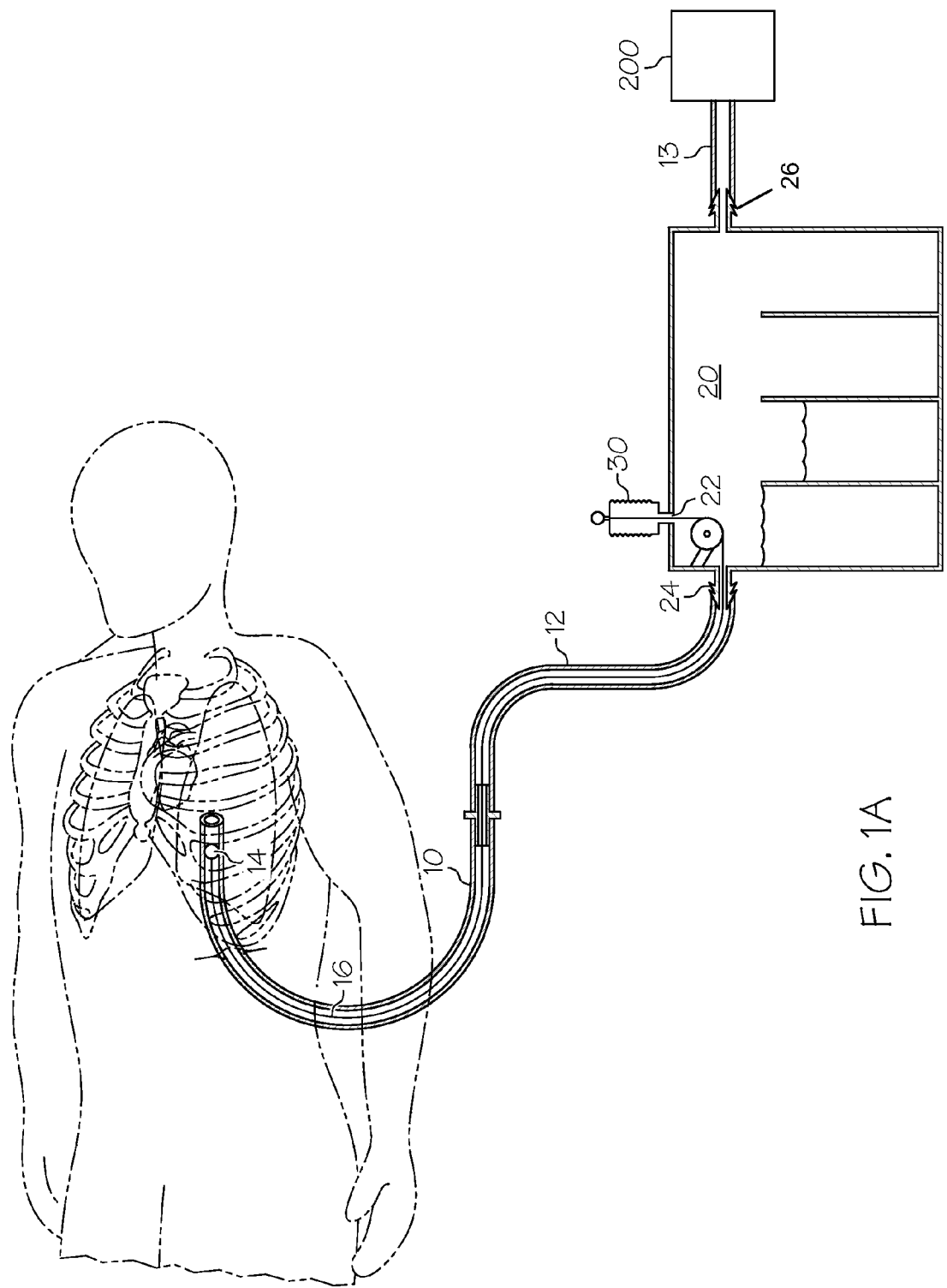
FIGS. 1a and 1b are schematic perspective illustrations showing a medical tube (a chest tube is illustrated) for draining material from a patient, which is coupled to a drainage canister and ultimately to a suction source. These figures show a clearance member at the end of a guide member for clearing obstructions from the medical tube, which is at different stages of actuation in the respective figures. The guide member extends back into the drainage canister and is coupled to a guide-member actuator at or adjacent its proximal end.

As used herein, the terms proximal and distal are generally to be construed with reference to a patient that has been or is to be fitted with a medical tube, such as a chest tube. For example, the distal end or region of a medical tube (e.g. chest tube) is that end or region that is to be inserted into or disposed more adjacent (e.g. within) the patient during use, as compared to the opposite end or region of the medical tube (chest tube). Similarly, a distal element (or the distal side or region of an element) is nearer to the patient, or to the distal end of the chest tube, than a proximal element (or the proximal side or region of an element). Also herein, the "terminal" end of a tube, wire or member refers to its distal end.

FIG. 1 shows a schematic representation of a medical tube being used to drain fluid accumulated fluid from within the body cavity of a patient, in accordance with an exemplary embodiment of the invention. In FIG. 1 the medical tube is inserted into and used to drain fluid from the chest cavity of the patient, and so is referred to as a chest tube 10. Chest tubes 10 are a common type of medical drain tube and the remaining description will be provided with reference to chest tubes 10. However, it is to be appreciated that the aspects and embodiments of the invention hereafter described can be applied directly or with minor and routine modifications to clear obstructive debris from different medical tubes used in different applications, for example catheters, surgical drain tubes to drain fluid from other orifices (besides the chest cavity), endotrachial tubes, feeding tubes, gastric tubes or tubes to deliver material to or from the alimentary tract, etc.

Returning to FIG. 1, the chest tube 10 enters the patient through the chest-cavity (body) wall, so that its distal end is positioned within the chest (body) at a location from which fluid is to be drained. The proximal end of the chest tube 10 remains outside the body. The chest tube 10 can be inserted into the patient in a conventional manner, and positioned and secured in place through the chest-cavity wall by the physician. The proximal end of the chest tube 10 is provided in fluid communication with a suction source 200 to draw fluid and other debris out from the chest tube 10. The suction source 200 also helps sustain the normal physiologic negative pressure within the chest of the patient. One or more drainage tubes 12 and/or drainage canisters 20, may be disposed intermediate the chest tube 10 and suction source 200, e.g. via a suction tube 13, in fluid communication therewith to provide a suction pathway from the chest tube 10 to the suction source 200. As used herein a drainage canister is a container, vessel or other enclosure that defines a volume or fluid chamber for the accumulation of debris and other material from a human or animal patient, which is capable of being provided in fluid communication with a medical tube to at least in part define a sterile field therewith. The drainage canister provides a storage volume for drained fluid and debris and thereby serves two functions in the disclosed embodiments. First, the drainage canister 20 protects the suction source 200 from being damaged or contaminated by an influx of drained fluids and other materials and secretions from the patient. Second, the canister 20 permits the clinician to visualize the volume of material drained from the patient.

In a preferred embodiment, a clearance member 14 is normally disposed within the chest tube at or proximate its distal end as seen in FIG. 1a. The clearance member 14 is formed at or attached to the distal end of a guide member 16 that can be inserted into and through the chest tube 10. To clear clot material or other obstructions that may form or accumulate within the chest tube 10 from time to time, in this embodiment the clearance member 14 is drawn proximally, via guide member 16, to catch and thereby also draw any such obstructions proximally through, and preferably out of, the chest tube 10. In preferred embodiments, the clearance member 14 can be drawn substantially toward the drainage canister 20, so that any obstructive materials mechanically engaged by the clearance member 14 can be drawn completely out of the chest tube 10 and any drainage tube 12 located between the chest tube and the canister 20.

As seen in FIG. 1a, with the clearance member 14 positioned adjacent the chest tube's distal end, the guide member 16 extends from the canister 20 all the way through the chest tube 10 and any drainage tube 12 therebetween. The proximal end of the guide member 16 is connected to a guide-member actuator 30. The actuator 30 is operable to actuate the guide member to reversibly withdraw the clearance member 14 from the distal end of the chest tube 10, thereby drawing clot material or other obstructions proximally through or out of the chest tube, and thereafter to re-insert the clearance member 14 so that it is located at its resting position adjacent the chest tube's 10 distal end. In an example embodiment, seen in FIG. 1b, the actuator 30 is operable to draw the clearance member 14 all the way back to the drainage canister 20, so that any obstructions carried out of the chest tube 10 by the clearance member are mechanically drawn all the way back to the canister. This embodiment may be preferred to reduce the incidence of clot or other obstructive material being entrained in the drainage tube 12 after it is drawn out of the chest tube 10.

Preferably, guide member 16 is in the form of a guide wire. The remainder of this description is provided with reference to a guide wire 16. However, other embodiments wherein a guide member that is not a wire can be used to reversibly advance the clearance member 14 through the suction pathway (defined herein) to clear debris. For example, other guide members that can be substituted for the guide wire 16 described herein include an elongate flat metal or plastic strip, or other elongate form, that is flexible but biased to a straight configuration but capable to negotiate bends in the medical tube (such as chest tube 10) and any intermediate drainage tube(s) 12 that may be used. Still further embodiments of a guide member that could be substituted for the guide wire 16 described herein, which will be readily ascertained by those having ordinary skill in the art, can be used.

Referring now to FIGS. 2a-b, an exemplary embodiment of a guide-member actuator 30 is shown schematically in cross-section. Throughout the remaining description, this is referred to as a guide-wire actuator, based on the preferred embodiment wherein the guide member is a guide wire 16. In this embodiment, the actuator 30 includes a handle portion 32 having an endcap member 32a, such as a disc member, and a handle 32b attached to a surface of the endcap member 32a. A flexible or collapsible sheath 34 is attached at its first end to the endcap member 32a and at its second end to the housing of the canister 20, or to an actuator seat 36 that is formed with or attached to the housing as seen in the figures, surrounding an actuator port 22 through the housing wall of the canister 20. The proximal end of the guide wire 16 extends from the actuator port 22 and is attached to the endcap member 32a within the sheath 34. Optionally, a wiping septum can be provided in the port 22 through which the guide wire 16 passes as it is advanced or withdrawn via the actuator 30. The sheath 34 is sealingly attached at either end to the endcap member 32a and the housing 20 (or optional seat 36) to protect the sterile field within the drainage canister 20, the chest tube 10 and any associated drainage tubes 12 during actuation of the guide-wire actuator 30 to insert or withdraw the guide wire 16 as explained herein.

Figure 1B:
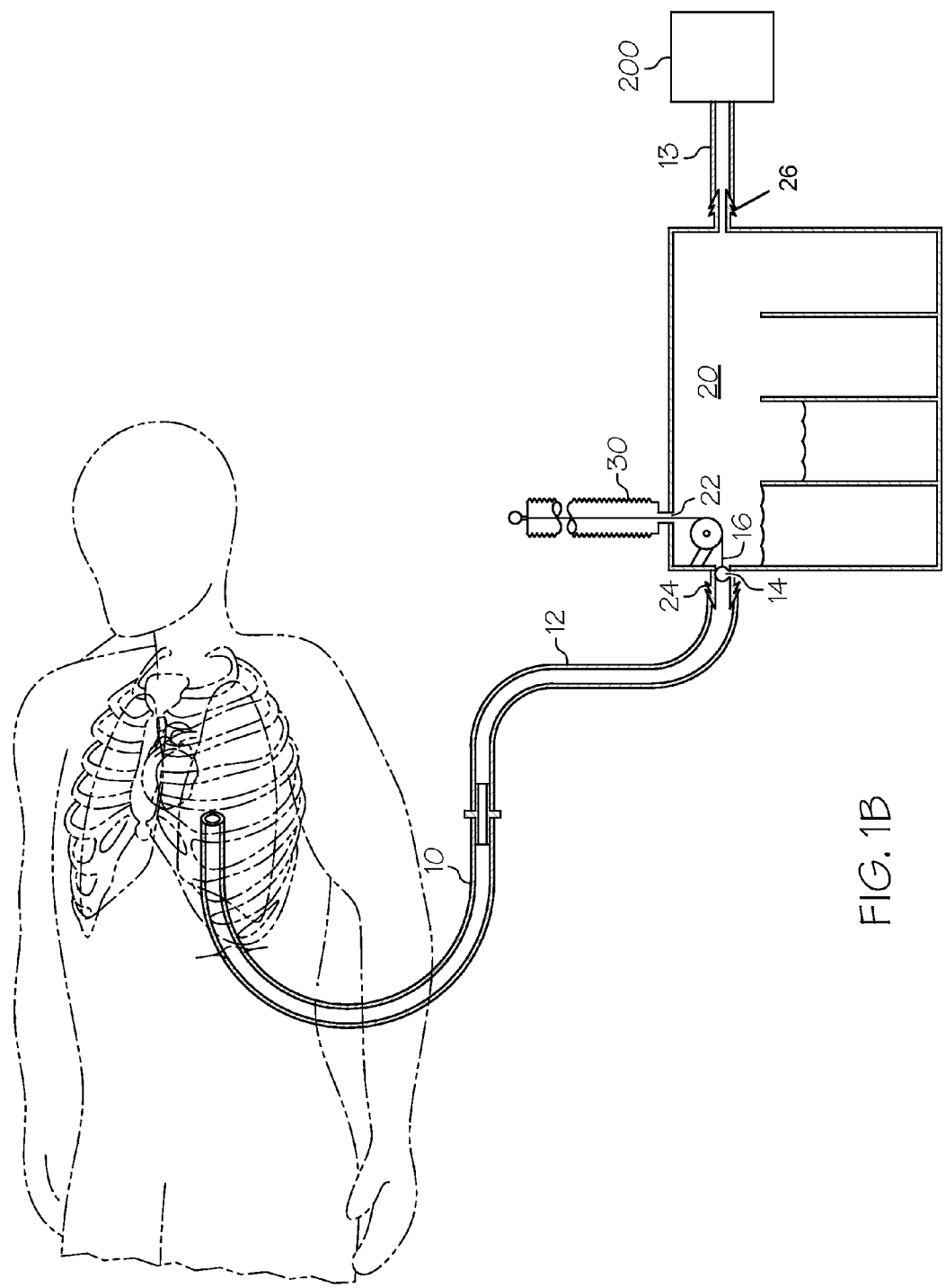

As seen in FIGS. 1-2 and explained above, the guide wire 16 extends from the endcap member 32a through the actuator port 22 in the canister 20 housing, then through drainage port 24 in the housing toward or through the chest tube 10 to manipulate the clearance member 14 disposed at its distal end. In FIG. 2a (corresponding to FIG. 1a), the actuator 30 is shown in a first position wherein the guide wire 16 is inserted to its maximum extent into and through the canister 20, and thereafter through the chest tube 10. In FIG. 2b (corresponding to FIG. 1b), the actuator 30 is shown in a second position wherein the handle 32b and proximal end of the guide wire 16 are withdrawn to a maximum extent from the canister 20 housing, with a substantial length of the guide wire 16 being now accommodated within the volume of the expanded sheath 34. As seen in FIG. 1b, in this embodiment the guide wire 16 can be withdrawn so the clearance member 14 is retracted to a position just proximate the drainage tube 12 within the canister 20. In another embodiment, the clearance member 14 can be retracted to a position just proximate the chest tube 10 within the drain tube 12 (not shown). In this latter embodiment, the canister 20 and drainage tube 12 can be supplied together, with the guide wire 16 in the fully-withdrawn position so that it and clearance member 14 initially are housed within the drainage tube 12 as-supplied. The drainage tube 12 can be plugged to ensure the interior of the canister and drainage tube 12 (as well as the guide wire 16 and clearance member 14) remain sterile until use.

Alternatively, the canister 20 can be supplied with the chest tube 10 and optionally an intermediate drainage tube 12 all linked in fluid communication. In this embodiment, the guide wire 16 and actuator 30 can be supplied initially in the fully-inserted position with the clearance member 14 disposed within the chest tube 10 just inside its terminal end. This embodiment may be desirable because then the length of the guide wire 16 can be supplied to correspond precisely to the length of the chest tube 10 and any intermediate drainage tube 12 that will be used.

Regardless which embodiment above is used, the length of the sheath 34 in the fully-expanded state can be selected beforehand so that it is supplied having a fully-expanded length that precisely corresponds to the length-extent to which guide wire 16 and clearance member 14 are to be permitted to be fully withdrawn. For example, if it is desired that the guide wire 14 can only be withdrawn from the chest tube 10 to a position just inside the drainage tube 12 proximal to the chest tube 10, then the sheath's 34 fully-extended length can be selected to correspond to just over the length of the chest tube 10. This is true regardless whether the chest tube 10 is to be supplied already connected to the drainage canister 20, together with the drainage canister 20 but not yet connected, or even separately, so long as the length of the chest tube 10 is known or is specified in the operating instructions that accompany the drainage canister 20. Alternatively, if it is desired that the clearance member 14 can be withdrawn through the chest tube 10 and any intermediate drainage tube 12 to just inside the drainage canister 20, then the sheath's 34 fully-extended length can be selected to correspond to just greater than the sum of the lengths of the tubes 10 and 12, either as-supplied with the drainage canister 20 or as otherwise specified.

In still a further alternative, the canister 20 can be supplied alone with the guide wire 16 fully withdrawn so that the clearance member 14 at its terminal end rests just within the fitting for attaching the drainage tube 12 or a chest tube 14 to the canister 20. If the chest tube 10 (and intermediate drainage tube 12, if present) are not supplied with the drainage canister 20 and their lengths are not specified, additional care may be necessary when using the actuator 30 to advance the guide wire 16 and clearance member 14 during use, because the extensible length of the guide wire 16 (or sheath 34) as-supplied may be greater than the lengths of the chest tube 14 and any intermediate drainage tube 12 that are to be connected thereto for use with a patient. It is contemplated that numerous different guide-wire lengths can be made available to correspond to a variety of chest-tube 10 and intermediate drainage-tube 12 combinations, which can be supplied either together with the canister 20 or separately.

Regardless which of the foregoing embodiments is selected, the length of the fully-expanded sheath 34 is preferably selected to correspond to the length of the guide wire 16 that is to be accommodated therein in the fully-withdrawn condition.

Optionally, a biasing member 38 can be provided to bias the actuator 30 in a normally-inserted (FIG. 2a) or a normally-withdrawn (FIG. 2b) position, depending on whether the guide wire 16 and clearance member 14 are to be normally positioned in the corresponding fully-inserted or fully-withdrawn position during use. When the clearance member 14 is to be normally positioned in a fully-inserted position, e.g. when it is to rest adjacent the distal end of the chest tube 10 when not being actively used, the biasing member 38 is such as to bias the guide-wire actuator 30 in the normally-inserted position of FIG. 2a. To draw the clearance member 14 proximally, an operator grasps the handle 32b and draws it away from the canister 20 housing to thereby draw the guide wire 16 and clearance member 14 proximally through (and possibly out of) the chest tube 10, against the biasing force of the biasing member 38. Once obstructions have been cleared, the biasing force of the member 38 draws the handle 32b of the actuator 30 back toward the normally-inserted position illustrated in FIG. 2a, collapsing the sheath 34 and resulting in re-insertion of the clearance member 14 into the chest tube 10 to its fully-inserted position. When such a biasing member is used, it may be desirable for the operator to maintain contact with and control of the handle 32b when re-inserting the guide wire 16, to avoid a rapid or sudden re-insertion through the chest tube, which may be painful or have other undesirable effects. Alternatively, the biasing member 38 could be biased to the normally-withdrawn position. Such a biasing member 38 will resist pressing the handle 32b toward the housing of canister 20 (and thereby insertion of the guide wire 16), and will bias the handle 32 (and guide wire 16) back to the withdrawn position once any insertion force has been removed.

The biasing member 38 preferably is a coiled spring. Coiled springs can be supplied in an expanded state where there is normally spacing between adjacent coils of the spring, wherein the spring will tend to resist compression and will re-expand after any compressive force has been removed. Such a spring would be useful to bias the guide-wire actuator 30 in a normally-withdrawn position. Coiled springs can also be supplied in a fully-compressed state, where adjacent coils of the spring are normally in physical contact, wherein the spring will tend to resist expansion and will re-compress after any expansive force has been removed. Such a spring would be useful to bias the guide-wire actuator 30 in a normally-inserted position. Regardless which of these two springs is used (depending on whether a normally-inserted or normally-withdrawn position for actuator 30 is desired), the spring is seated in and preferably attached to an actuator seat 36 that is attached to the housing of the canister 20, or otherwise formed therewith, which surrounds the actuator port 22. Alternatively, the spring or other biasing member 38 can contacted or be attached directly to the housing wall surrounding the port 22, with no seat 36 or other distinct structure provided. The opposite end of the spring is contacted or attached to the endcap member 32a of the handle portion 32. In the illustrated embodiments, the flexible sheath 34 surrounds the biasing member 38 as well as the portion of the guide wire extending from the port 22. Alternatively, however, the biasing member can be provided outside the sheath 34, such that the sheath 34 only encloses the portion of the guide wire 16 extending from the actuator port 22 to maintain a sterile field (not shown).

All portions and spaces of the canister 20, including actuator 30, that will be exposed to the guide wire 16 or otherwise be in fluid communication with the suction pathway during use are sterile as-supplied. Herein, the suction pathway is defined by the chest tube 10, the canister 20 housing and any associated drainage tubes 12 and suction tubes 13 that are provided in-line between the chest tube 10 and the suction source 200.

The materials of construction of the guide wire 16 and clearance member 14, as well as the configuration of the clearance member 14, are not critical to the present invention. In desirable embodiments, the guide wire 16 and clearance member 14 may be constructed and configured as follows.

The clearance member 14 can be reversibly advanced into and through the chest tube 10 via advancement and withdrawal of the guide wire 16 to which it is attached to withdraw obstructive debris from the chest tube as described above (and further described below). The clearance member 14 is preferably disposed in and secured to the distal region of the guide wire 16, preferably at its distal end. In one embodiment, the clearance member 14 can be formed by the guide wire. For example, the terminal end of the guide wire can be wound to form a loop 124a at its terminal end.

Figure 3B:
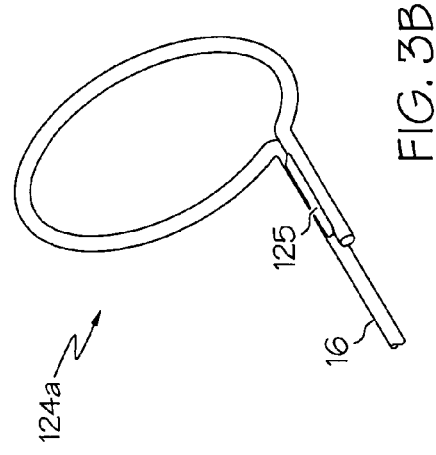
FIGS. 3a-3d illustrate various embodiments of a clearance member disposed at the distal end of a guide member, as well as an embodiment of the guide member in the form of a guide wire having a core-and-sheath construction (FIG. 3d).
Figure 3D:
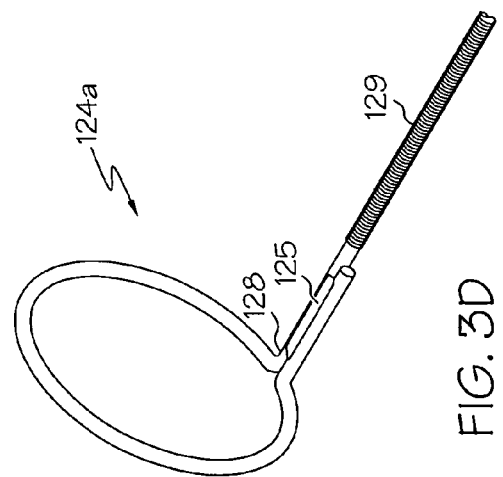
Figure 3A:
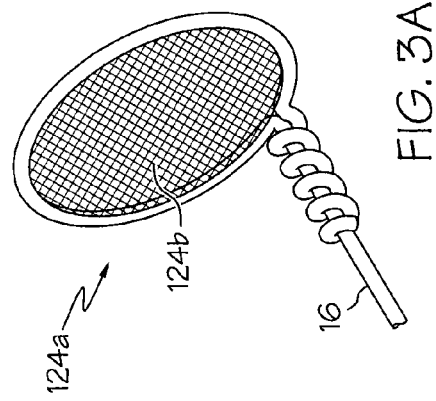

FIG. 3a illustrates one embodiment using a guide wire 16 where the terminal portion of the guide wire 16 is wound to form loop 124a. A small amount of slack after forming the loop 124a in this embodiment is wound tightly along the length of the wire 16 immediately proximal to the loop 124a. The amount of slack to be so wound can be, e.g., about or less than the diameter of the loop 124a, or about or less than twice that diameter. When so wound, the slack is preferably wound so that adjacent turnings of the slack over the guide wire 16 are immediately adjacent (preferably in or nearly in contact with) one another, and substantially fully in contact with the portion of the wire 16 over which they are wound.

Figure 3C:
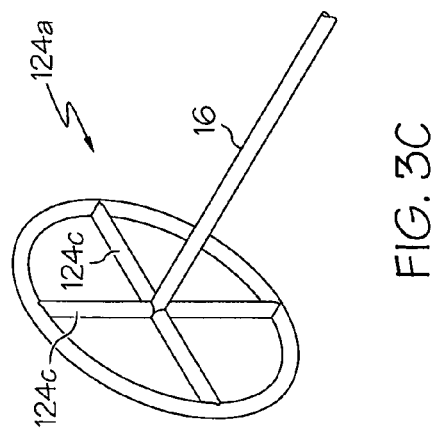

In another embodiment illustrated in FIG. 3b, the slack in the wire 16 after forming loop 124a can be soldered to the portion of the wire 16 immediately proximal to the loop 124a at solder joint 125. The slack can be positioned parallel to the portion of the guide wire 16 to which it is to be soldered, as shown in FIG. 3b. Alternatively, it may be wound around the guide wire 16 and then soldered. The length of the slack can be similar as described above with respect to FIG. 3a. Alternatively, if the slack is to be soldered in parallel to the wire 16 as seen in FIG. 3b, it is preferable that its length be about or less than one radius (½ the diameter) of the loop 124a. The diameter of loop 124a is preferably selected to substantially correspond to the diameter of the inner wall of the chest tube 10 in which the loop 124a (clearance member 14) will be used, as described in more detail below. Optionally, though perhaps less preferred, a mesh 124b (seen schematically in FIG. 3a) can be provided extending across the diameter of the loop 124a, having openings dimensioned to permit fluid to flow therethrough. In this embodiment, liquid-phase blood and other fluids will be permitted to pass through the mesh 124b from the body cavity, into the chest tube 10 from the opening at its terminal end. Thereafter, should such blood or other fluid form a clot in the chest tube 10, the mesh can assist to draw the clot out of the chest tube 10 upon withdrawal of the loop 124a proximally, as described above and in more detail below. The guide wire 16 can be attached at the perimeter of the loop 124a, and can be formed integrally with the loop 124a. Alternatively, the guide wire 16 can be attached at the center of the loop 124a via cross members 124c as seen in FIG. 3c. However, embodiments that include elements that obstruct the opening at the center of the loop 124a (e.g. mesh 124b or cross members 124c) are less preferred due to the potential to promote obstruction of the loop 124a, e.g., by the formation of clot material attached to such elements.

As seen in FIGS. 3a-3d, the loop 124a lies in a plane that is at a predetermined angle, for example 90°, to the longitudinal axis of the guide wire 16 at the point where the loop 124a and guide wire 16 (e.g. the longitudinal expanse of the guide wire 16 if that wire is used to form the loop 124a) intersect. The precise angle may be subject to some variance, for example due to flexure of the guide wire 16 and loop 124a as they are advanced and/or drawn through the chest tube. Preferably the angle between the loop 124a and guide wire 16 is in the range of 75° to 105°, more preferably 80° to 100°, more preferably 85° to 95°.

The guide wire 16 can be made from conventional materials including plastics and metals. It is preferred that the guide wire 16 be made from a material having sufficient flexibility that it can reversibly bend to a radius of curvature of four centimeters, more preferably three centimeters, more preferably two centimeters or one centimeter, without snapping or substantially compromising its structural integrity. Suitable materials include nitinol, stainless steel and titanium-nickel alloys. In addition to being sufficiently flexible to negotiate bends in the chest tube 10 (or drainage tube 12) on being advanced/retracted therethrough, the guide wire 16 should have sufficient stiffness or rigidity to be pushed through accumulated clot material within either tube without kinking or being caused to double back on itself.

The requisite flexibility to negotiate bends simultaneous with the requisite stiffness to be pushed through clot material may be achieved by biasing the flexible guide wire 16 to a generally straight (linear) configuration. This can be achieved, for example, utilizing a core-and-sheath construction as illustrated in close-up view in FIG. 3d. In this figure, the guide wire 16 includes a core wire 128 and a sheath wire having a smaller diameter than the core wire 128 wound around the core wire 128 to provide a spiral-wound wire sheath 129. The wire sheath 129 can be made from any suitable material, e.g., including the same or similar materials useful for the core wire, noted above.

The wire sheath 129 will tend to bias the guide wire 16 (including core wire 128 and sheath 129) into a straight or linear configuration, while still permitting the wire 16 to bend in order to traverse bends in the chest tube 10 when in use. In this embodiment, the guide wire 16 (including core wire 128 and sheath 129) still preferably can be bent to the radii of curvature noted above without snapping or substantially compromising its structural integrity. In a preferred embodiment, the sheath 129 stops short of the distal end of the guide wire 16, where the core wire 128 emerges unsheathed and is formed into the loop 124a at its distal end. In the embodiment shown in FIG. 3d, the slack in the core wire 128 after forming loop 124a is soldered to the portion of the core wire 128 immediately proximal to the loop 124a at solder joint 125, similar as in the embodiment described above with respect to FIG. 3b. However, other modes of forming and securing the loop 124a from the terminal or distal portion of the core wire 128 may be employed. In one embodiment, not shown, the loop 124a may be formed from the complete core-and-sheath construction of guide wire 16, wherein the sheath 129 continues around the loop 124a. Alternatively, a separate clearance member 14 may be secured at or in the vicinity of the distal end of the guide wire 16, whether a sheath 129 is employed or not.

Optionally, whether a sheath 129 is employed or not, the guide wire 16 may be coated substantially along its length with a friction-reducing material, to help prevent agglomeration of debris (such as blood clots) to the guide wire, and also to assist in transitioning the guide wire around bends in a chest tube 10 where it is to be inserted. Suitable coating materials for this purpose include, e.g., Teflon (polytetrafluoroethylene) compositions, polyurethane compositions, other hydrophilic polymers, and other coatings, including coatings comprising therapeutic agents such as a heparin coating or antibiotic coating.

Referring again to FIGS. 1a-1b, a chest tube is connected in fluid communication with a drainage canister 20 and a suction source 200, with a clearance member 14 disposed in the chest tube 10 to clear debris therefrom. The clearance member 14 is attached to or disposed in the distal region or at the distal end of a guide wire 16. The chest tube 10, intermediate drainage tube 12 and canister 20 are provided in fluid communication with one another to define the suction pathway described above via fluid-tight connections or seals that are effective to maintain a sterile field within the suction pathway. Such connections may include, for example, conventional barbed fittings as known in the art. The chest tube 10 (or intermediate drainage tube 12 if present) is secured to a drainage port 24 that provides fluid communication with the interior of the canister 20. Separately, the vacuum source 200 is connected via a vacuum tube 13 to a vacuum port 26 of the canister 20, which also provides fluid communication to the interior of the canister 20. Preferably, the drainage and vacuum ports 24 and 26 are located distant from one another, and both preferably above the intended maximum liquid level in the canister for drainage. The guide wire 16 extends from its proximal end attached to the actuator 30 through the drainage port 24 of the canister 20, and into the chest tube 10 where the clearance member 14 is used to dislodge obstructive material. As explained above, the guide wire 16 is actuable via the guide-wire actuator 30 to reversibly insert and withdraw the clearance member 14 through the chest tube 10 to clear debris that has accumulated therein.

Preferably, the chest tube 10 and any intermediate drainage tube 12 are made from materials having elastic properties, such as silicone, which will help ensure a fluid-tight seal because the tubes 10,12 will tend to contract over the barbs of barbed fittings. A flexible, elastic chest tube 10, e.g. made from silicone, also will result in reduced discomfort for the patient compared to more rigid chest-tube materials, such as polypropylene or polyethylene. However, if desired these and other rigid materials may be used. Other elastic materials, including elastic thermoplastics, also may be used in place of silicone, if desired. Preferably, the chest tube 10 is made from a clear (i.e. transparent or substantially transparent) plastic material, so the operator can visualize any clot material or other debris therein, as well as its removal as described below. In embodiments, the chest tube 10 can be made of a soft material such as silicone to improve patient comfort, while the intermediate drainage tube 12 can be made of more rigid, less expensive materials including those described above.

As seen in FIG. 4, the chest tube 10 can have one or a plurality of apertures 119 through the wall of the tube 10 in the distal region thereof, to assist in suctioning and drawing fluid located in the body cavity where the chest tube 10 is placed. Preferably, the clearance member 14 is dimensioned and oriented so that it cannot pass through the apertures 119, to emerge laterally from the chest tube 10. In the illustrated embodiment, the diameter of the wire loop 124a (or other clearance member 14) is too large to fit through the width of apertures 119 based on its orientation, which is fixed relative to the guide wire 16. In addition, it may be desired that the length of apertures 119 also be smaller than the loop 124a diameter. As also seen in FIG. 4, optionally there can be one or more additional clearance members 124e disposed along the length of the guide wire 16 between the distal clearance member 14 and the proximal region of the guide wire 16, to help dislodge clots and other debris along the length of the chest-tube passageway 116, for example via a back-and-forth motion of the guide wire 16.

In operation, with the chest tube 10 (its distal end) inserted in a body cavity of a patient and being connected to a drainage canister 20 at the opposite end, and further with a suction source 200 being connected with the thusly defined suction pathway, fluid from the body cavity is drawn into and through the chest tube 10, then through the drainage tube 12 to be collected in the drainage canister 20. In the illustrated embodiments, the clearance member 14 is in the form of a wire loop 124a. The diameter of the wire loop 124a preferably substantially corresponds to the inner diameter of the chest tube 10, such that the loop 124a scrapes the inner diameter 14 as it translates along the chest-tube 10 length. The diameter of the wire itself that forms the wire loop 124a is very small, preferably about or less than 10%, preferably 8%, preferably 6%, preferably 5% or 4%, the inner diameter of the chest tube 10, to provide a substantially unobstructed pathway from the distal end of the chest tube 10 into and through its chest tube 10, through the loop 124a. Fluid and other debris drained from the body cavity pass into the chest tube 10, through the loop 124a, and proceed proximally toward the suction source 200. As such fluid moves through the chest tube 10, particularly fluids comprising blood or platelets, the fluid can form or produce clots that stick to the inner wall of the chest tube 10 (FIG. 1a). As the clots form or build, they begin to obstruct the chest tube 10, inhibiting drainage. If left unchecked, such clots may completely obstruct the chest tube 10, rendering the chest tube 10 inoperative.

As noted above, in preferred embodiments the clearance member 14 (e.g. loop 124a) is normally disposed adjacent the distal end of the chest tube 10 inside the chest tube 10. This position of the clearance member 14 corresponds to the fully-inserted position of the guide-wire actuator 30 as illustrated in FIG. 2a. To help clear the chest tube 10 of clots and other debris accumulated therein, a nurse, physician or other operator grasps the handle 32b of the actuator 30 and pulls it away from the housing of canister 20. This in turn draws the guide wire 16, which also draws the clearance member 14 proximally through the chest tube 10 as seen in FIG. 1b. As the clearance member 14 is drawn proximally, it engages clot material and other debris in its path and forces such material and debris proximally, toward the drainage canister 20. If desired, the operator can translate the clearance member 14 back-and-forth within the chest tube 10 (and optionally the drainage tube 12) through back-and-forth translation of the handle 32b of the guide-wire actuator 30 toward and away from the drainage canister 20. This may help break up clot material or other debris, as well as aid in drawing such debris proximally. At the conclusion of the clearance operation, the operator can re-insert the clearance member 14 to its resting position (assuming a normally-inserted configuration is used) by fully advancing the handle 32b of the actuator 30 toward the canister 20 (FIG. 2a). Such re-insertion may be effected or assisted by an appropriate biasing member 38, if present, as explained above.

Alternatively, in the case where the guide-wire actuator 30 is to be in a normally-withdrawn position, so that in the parked position of the clearance member 14 is distant from the chest tube's 10 distal end, to clear debris from the chest tube 10 the handle 32b of actuator 30 is pressed toward the canister 20, thus compressing the sheath 34 and inserting the guide wire 16 and clearance member distally 14 through the chest tube 10. In this embodiment, the clearance member is initially advanced distally so that it approaches the distal end of the chest tube 10, preferably past any debris therein, before being withdrawn again proximally to draw debris out of the chest tube 10. This embodiment is less preferred, because it may result in advancing debris out of the distal end of the chest tube 10 when the clearance member 14 is first advanced therein from its resting position.

Optionally, the inner diameter of the drainage tube 12 can be larger than the inner diameter of the chest tube 10. In this embodiment, debris removed from the chest tube 10 and into the drainage tube 12 will be less obstructive in the drainage tube 12 and more readily drawn out and into the canister 20 via suction applied by the suction source 200. Alternatively, a drainage tube 12 that eventually becomes fully obstructed will be more readily and easily replaced than a chest tube, which is surgically implanted through the patient's body wall and would require revision surgery, and additional opportunity for injury and infection, to replace. If the drainage tube 12 is to be replaced, requiring breaking the sterile field within the suction pathway, care should be taken to establish a sterile field around the breakage point (i.e. between the chest tube 10 and canister 20) when substituting a new drainage tube 12.

Figure 5:
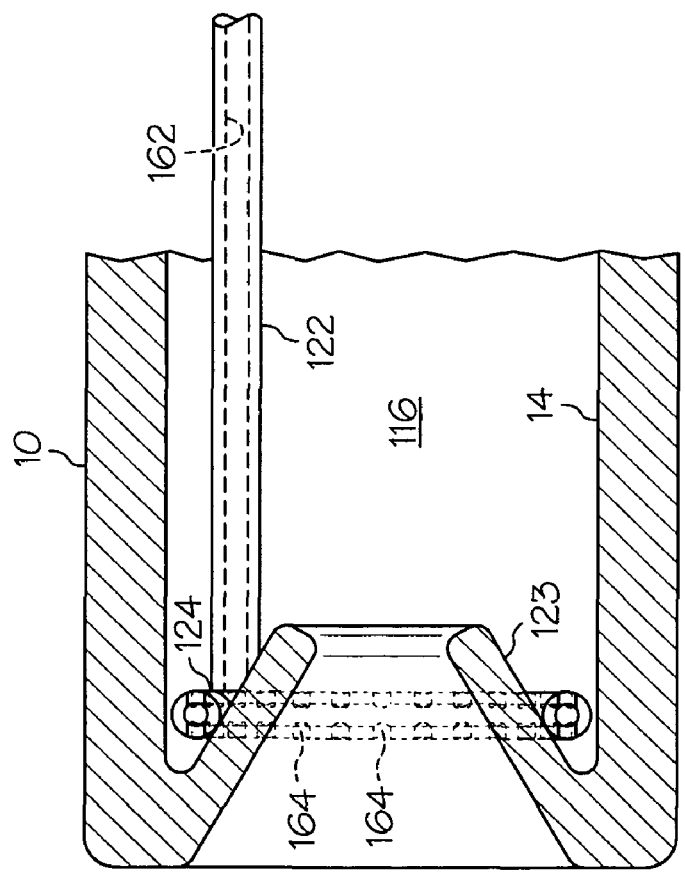
FIG. 5 is a side view, partially in section, of the distal region of a medical tube according to an embodiment hereafter described, which includes a clearance-member seat disposed at the distal end of the medical tube.

In one embodiment illustrated in FIG. 5, the chest tube 10 can include a conical clearance-member seat 123 extending radially inward and in a proximal direction from the distal end of the chest tube 10, within the chest-tube passageway 116. In this embodiment, when a clearance member in the form of loop 124a is seated at the distal end of the chest tube 10 after use, as by replacing the handle 32b of the guide-wire actuator in the inserted position (FIG. 2a), the seat 123 projects through the clearance-member loop 124a, thereby dislodging any clot material that may be adhered to the loop 124a. In certain embodiments, such a clearance-member seat 123 may be less preferred due to a tendency to increase the incidence of clogging the entrance to chest tube 10 at the distal end of the chest tube 10.

In a further embodiment, the guide wire (or more generally guide member) 16 can have a guide lumen 162 provided in fluid communication with one or more openings 164 disposed through the wall of the loop 124a (or other clearance member 14). The guide lumen 162 and cooperating openings 164 may be utilized to deliver flushing or irrigation fluid to assist in dislodging any material stuck to the clearance member loop 124a. In addition or alternatively, fluid expelled from guide lumen 162 through openings 164 may be a solution provided to assist in the dislodgment, dissolution and/or breakup of the debris. To deliver fluids into the guide lumen 162, a fluid port can be provided in fluid communication therewith near the proximal end of the guide wire 16, for example through the endcap member 32a or through the sheath 34 (not shown). The fluid port can have a conventional receiver on the outside to mate with a syringe or other fluid-delivery device, to communicate a fluid from the delivery device through the flexible tubing, and into and through the guide lumen 162 to emerge through openings 164. Fluids suitable for the particular purpose include, but are not limited to, anti-thrombolytic agents, Alkalol™, among others. In still other embodiments, such fluid may be or include a therapeutic agent such as but not limited to antibiotic agents, anti-neoplastic agents, and other agents for a variety of purposes, including pain relief, treatment of infection, cancer, or to induce scarring (i.e. pleurodesis). Alternatively to delivering a fluid the guide lumen 162 can be utilized to draw a vacuum at the openings 164 provided at the distal end of the guide wire 16 by applying a vacuum to the fluid port at the proximal end of the guide wire 16.

Alternatively to delivering fluids, the guide lumen 162 may be used to detect carbon dioxide in the chest cavity as a means to determine whether there is a puncture in a patient's lung. In this mode of operation, a $CO_2$-sensing instrument or appropriate litmus paper that can sense the presence of $CO_2$, e.g. via a color change, can be connected in fluid communication with the aforementioned fluid port outside the guide-wire actuator 30. This instrument/litmus paper may be provided outside the sterile field in communication with the fluid port or receiver mentioned above. Alternatively to sensing $CO_2$ through the guide lumen 162, it may be more desirable to instead provide $CO_2$-sensing equipment in communication with the lumen of the chest tube 10 to sense the presence of $CO_2$ in the chest tube. This can be achieved, for example, by placing a $CO_2$-sensor, such as a sensing transducer or a holder for $CO_2$-sensitive litmus paper, in-line between the chest tube 10 and the suction source 200, for example between the drainage tube 12 and chest tube 10, or within the canister 20, such as CO2-sensor 50 shown schematically in FIG. 7. In this embodiment, $CO_2$ passing from the chest tube 10 to the suction source will pass through the $CO_2$ sensor, permitting the sensor to alarm if $CO_2$ is detected. In a further alternative, the $CO_2$ sensor may be coupled to the chest tube lumen via a lateral channel in communication with the chest tube (not shown).

As mentioned previously, it is conventional to select relatively large-diameter chest tubes 10, or to place more than one tube, to provide excess drainage capacity as a hedge against the formation of clots, which may obstruct drainage. A common size for a conventional chest tube 10 is 32-French. When used with such a chest tube 10, the drainage tube 12 between the chest tube 10 and the drainage canister 20 (when used) preferably is larger, so as to have a larger inner diameter, for example 30-French or 28-French. However, it is preferable to select chest tubes 10 having the smallest practical diameter while still achieving reliable drainage. Using a clearance member 14 that is actuable via a guide-wire actuator 30 as disclosed herein, it is believed that reliable drainage will be possible due to the ability to reliably clear clot material that might otherwise obstruct the chest tube 10. As a result, it is contemplated and preferred that smaller chest tubes 10 will be used, for example preferably smaller than 32-French, e.g. 34- to 36- or 38-French. In all cases, the drainage tube 12 intermediate the chest tube 12 and the drainage canister 20 preferably has a larger inner diameter than the chest tube 10, preferably at least two French sizes larger. Also preferably, the clearance loop 124a is selected so that its loop diameter substantially corresponds with the inner-wall diameter of the chest tube 10 that is selected.

Figure 6:
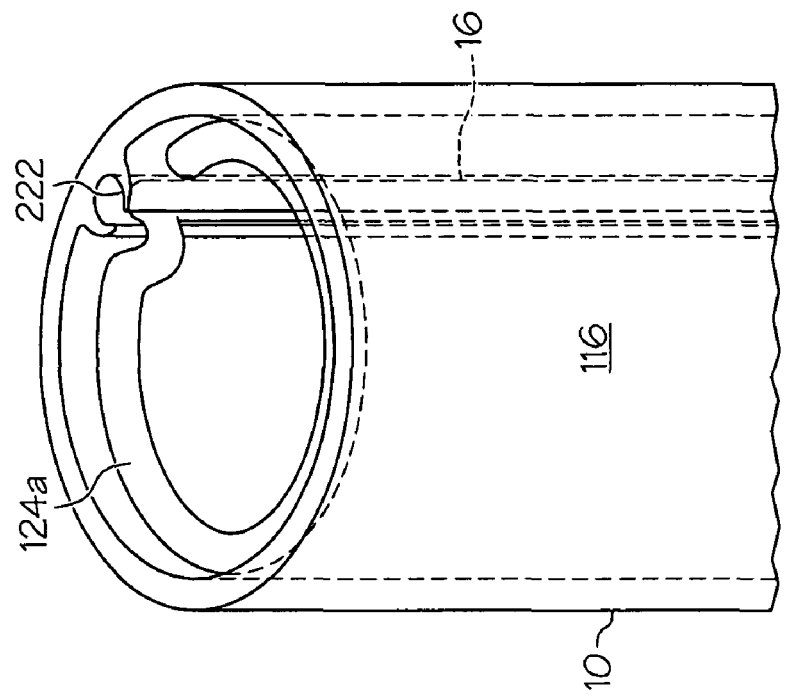
FIG. 6 is a perspective view of the distal region of a medical tube according to a further embodiment hereafter described, which includes a slot disposed in the inner wall of the medical tube that is adapted to house and accommodate the guide member as it translates along the axis of the medical tube.

In the embodiments already discussed and illustrated in the aforementioned figures, the chest tube 10 has a single inner lumen defined by its inner diameter, which has a circular cross-section. In a further embodiment illustrated in FIG. 6, the inner surface of the chest tube 10 wall has a substantially circular cross-section but also defines a slot 222 extending longitudinally along the length of the chest tube 10, to accommodate the guide wire 16 therein. The guide wire 16 terminates at its distal end in a modified loop 124a whose shape preferably corresponds substantially to the cross-section of the inner surface of the chest tube 10 wall, having the slot 222 therein. This embodiment may be desirable in applications where the chest tube 10 may undergo relatively sharp bends, so that the slot 222, which houses the guide wire 16, can help prevent buckling of the wire 16 on advancement thereof. In this embodiment, it is desirable that the clearance member (loop 124a) not be fully withdrawn out of the chest tube during use, due to the difficulty to re-align the guide wire 16 with the slot 222 to reinsert the same once it has been withdrawn.

As noted above, the medical tube need not be a chest tube. The drainage canister 20 disclosed herein, having a guide-wire actuator 30 to controllably advance and withdraw the guide wire 16 and clearance member 14, can be used in conjunction with other medical tubes used to provide fluid communication between a location within a human or animal body and an external apparatus or environment, either to drain fluid or other material from the body (e.g. chest tube, urinary catheter or other drainage tube) or to deliver material from outside the body (e.g. NG-tube or intubation tube).

As noted above, the medical tube (such as a chest tube 10 or other medical tube) can be provided with a lateral channel (or channels) for a variety of purposes, for example where it is desirable to have an additional access port into the medical tube, or into the body cavity where the distal end of the medical tube resides, such as to deliver medication. For example, in one embodiment a medication can be delivered to the patient's body cavity by inserting a small catheter through the lateral channel in communication with the medical tube, and snaking the catheter up through the medical tube (e.g. chest tube 10) until it reaches or, if desired, just emerges from the distal end thereof. Then a syringe or other delivery device connected to the proximal end of the catheter can be used to deliver the medication or other fluid through the catheter and into the body cavity where the distal end of the medical tube has been placed. The lateral channel in communication with such medical tube can be sealed via a suitable closure, such as a conventional valve, stopcock or septum, to permit insertion of a catheter when desired while maintaining a sterile field within the suction pathway. Such a lateral channel may be formed directly with the medical tube, or it may be provided in conjunction with an adapter disposed in-line with the suction pathway (such as a y-adapter placed between the tubes 12 and 14, or between tube 12/14 and the canister 20).

In an embodiment, a guide wire manipulation device can be used to impart vibrations or other energy or motion to the guide wire, and consequently to the clearance member 14 located at its distal end. Such a manipulation device can comprise, for example, a sonic transducer 40 coupled to an ultrasonic wave guide 45 as seen schematically in FIGS. 2a-2b. In embodiments, the sonic transducer or wave guide can be or form part of or couple to the handle portion 32 of the guide-wire actuator 30, to which the proximal end of the guide wire 16 is attached. In this embodiment, energizing the transducer will impart the corresponding vibrations or movement to the guide wire 16, which will in turn be transmitted along the guide-wire length and to the clearance member 14. In this manner, sonic or other vibrations generated by the transducer at handle portion 32 are conducted through the guide wire 16 and to the clearance member 14, to induce sonic motion to that member (e.g. loop 124a) as well as any surrounding fluid, further assisting in the breakup and/or dislodgment of any foreign or obstructing material in the chest tube 10. Alternative to sonic energy, the transducer can impart other forms of energy, such as sub-sonic vibrations, acoustic pulses, or even full or partial (e.g. back-and-forth or 'whipping') rotation to the wave guide attached to or forming part of the handle portion 32, which in turn will communicate the associated vibrations, or rotations to the guide wire 16 and ultimately to the clearance member 14 to assist in breaking up any debris. In these embodiments, the handle 32b preferably is insulated from any such vibrations or motion to protect the operator, and also so the handle 32b will not experience any such rotations or vibrations, which may inhibit its use by the operator. For example, a suitable gasket or other vibration-damping material can be provided intermediate the handle 32b and endcap member 32a, or a rotatable joint can be provided therebetween, enabling the endcap member 32a to rotate while the handle 32b is held rotationally steady.

By coupling the transducer or wave guide of the manipulation device to the handle portion 32 of the guide-wire actuator 30, the manipulation device can be operated outside the sterile field and will not compromise the sterile environment within the suction pathway when in use.

Thus far, the description has been provided in connection with the embodiment of a guide-wire actuator 30 as seen in FIGS. 2a-2b. However, numerous alternative embodiments of a guide-wire actuator could be employed and will become evident to persons of ordinary skill in the art who have reviewed this specification. For example, an alternative embodiment guide-wire actuator 30 is illustrated in FIG. 7. In this embodiment, the proximal end of the guide wire 16 is attached to a rotatable wheel or spindle 31 that is rotatably mounted inside the drainage canister 20. The guide wire 16 extends from its point of attachment to the spindle 31, through the canister 20 housing, and through drainage tube 12 on its way to a chest tube 10, wherein a clearance member 14 for clearing the chest tube 10 of debris is secured or formed at the distal end (or in the distal region) of the guide wire 16. In this embodiment, a hand-crank 33 is rotationally coupled to the spindle 31 through the housing wall of canister 20, such that an operator can manually rotate the spindle 31 to wind or unwind slack of the guide wire 16 therearound. As will be appreciated, this will have the effect to advance or withdraw the guide wire 16 from the chest tube 10/drainage tube 12, thereby actuating the clearance member to remove debris as already described. If desired, a torsion spring (not shown) can be utilized to bias the spindle 31 in one rotational direction or the other as desired, to provide either a normally-inserted or a normally-withdrawn guide wire 16/clearance member 14 as may be desired. In addition, an appropriate rotation-stop can be incorporated to ensure the spindle 31 does not rotate too far in one or the other direction, for example so that the guide wire 16 cannot be completely withdrawn into the drain canister. The rotational linkage through the housing wall between spindle 31 and crank 33 is provided so as to ensure and maintain the sterility of the drain canister 20 and suction pathway.

In still other embodiments the guide-wire actuator 30 can include other mechanical structure to advance and/or withdraw the guide wire 16 through the drainage port 24. For example, the handle portion 32 in the embodiment of FIGS. 1 and 2 may be replaced with a foot pedal coupled to the proximal end of the guide wire 16 to draw it out of the actuator port 22. Appropriate pulleys can be used, as known in the art, to string the guide wire 16 along an appropriate path depending on the geometry and location of the pedal structure, which is well within the ability of a person having ordinary skill in the art. In further alternatives, the drainage canister may include a trolley coupled to the proximal end of the guide wire, which is housed within the canister 20. The trolley can be slidably mounted or coupled to a side wall of the canister, within the interior of canister 20, and be adapted to translate along the canister wall in a vertical or other direction. This trolley may be coupled to a foot pedal, handle or other mechanism through the canister wall in a manner so as to ensure the sterility of the interior environment. The trolley then can be actuated to reversibly advance or withdraw the guide wire 16 through the drainage port 24 as already described. Alternatively, other wind-up mechanisms beyond that illustrated in FIG. 7 and described above might be used. In such mechanisms, torsion springs or other biasing members can be incorporated so that once a catch is released a winding or rotating element is caused to automatically rotate until it contacts or actuates a stop to cease its rotation or winding of the guide wire 16 (similar to a window shade roller). Optionally, the actuator 30 may comprise or be coupled to a mechanism to automatically actuate the guide wire/clearance member to remove debris from the chest tube 10 (or other medical tube) according to a fixed schedule, such as every 30 minutes, every hour, or another selected time interval.

Although the invention has been described with respect to certain preferred embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. A device for clearing obstructions from a medical tube, comprising a drainage canister having a drainage port for the introduction of material into the canister, and a vacuum port for connecting to a vacuum source to draw a suction through said canister, a guide-member actuator, and a guide member extending through said drainage port, said guide-member actuator being operable to advance and/or withdraw said guide member through said drainage port, said guide-member actuator comprising a biasing member to bias said actuator in either a normally-inserted position wherein the guide member is advanced to a maximum extent through said drainage port, or a normally-withdrawn position wherein the guide member is withdrawn to a maximum extent through said drainage port.

2. The device of claim 1, said guide member having a clearance member formed or attached thereto in a distal region thereof.

3. The device of claim 1, further comprising a medical tube in fluid communication with said drainage port, said guide member being at least partially received within said medical tube.

4. The device of claim 3, said medical tube being a chest tube.

5. The device of claim 3, said guide member having a clearance member formed or attached thereto in a distal region thereof, said clearance member being received within said medical tube.

6. The device of claim 3, said guide member being a guide wire, said clearance member comprising a loop that is formed at the distal end of said guide wire.

7. The device of claim 1, said guide-member actuator comprising a handle portion disposed outside said drainage canister, said guide member extending through an actuator port through a housing of said canister and being attached to said handle portion in a proximal region of said guide member.

8. The device of claim 7, further comprising a flexible sheath having a first end and a second end, the first end of said sheath being attached to said handle portion and the second end of said sheath being attached to an outer surface of said housing and surrounding said actuator port, said sheath enclosing a portion of said guide member that extends outside of said housing through said actuator port.

9. The device of claim 7, further comprising an actuator seat attached to or formed with said housing surrounding said actuator port, and a flexible sheath having a first end and a second end, the first end of said sheath being attached to said handle portion and the second end of said sheath being attached to said actuator seat, said sheath enclosing a portion of said guide member that extends outside of said housing through said actuator port.

10. The device of claim 8, further comprising a medical tube in fluid communication with said drainage port along a suction pathway, said flexible sheath having an expanded length that is approximately equal to the distance between said drainage port and a distal end of said medical tube along said suction pathway.

11. The device of claim 9, further comprising a medical tube in fluid communication with said drainage port along a suction pathway, said flexible sheath having an expanded length that is approximately equal to the distance between said drainage port and a distal end of said medical tube along said suction pathway.

12. The device of claim 1, said actuator comprising a spindle that is rotatably mounted inside the drainage canister, a proximal end of said guide member being attached to the spindle.

13. The device of claim 12, further comprising a hand-crank located outside said housing and rotationally coupled to said spindle through the housing.

14. The device of claim 12, said biasing member biasing the spindle against rotation in one rotational direction.

15. The device of claim 1, said guide member being flexible but biased to a straight configuration.

16. The device of claim 1, said guide member being a guide wire comprising a core wire and a sheath wire wound around the core wire to provide a spiral-wound wire sheath.

17. The device of claim 1, said guide member having a clearance member disposed at its distal end and having a guide lumen extending along its length and being in fluid communication with one or more openings disposed through a wall of said clearance member, said guide lumen being adapted to deliver fluid so that said fluid is expelled through said openings.

18. A device for clearing obstructions form a medical tube, comprising a drainage canister having a drainage port for the introduction of material into the canister, and a vacuum port for connecting to a vacuum source to draw a suction through said canister, a guide-member actuator, a guide member extending through said drainage port, said guide-member actuator being operable to advance and/or withdraw said guide member through said drainage port, and a $CO_2$-sensor to detect the presence of $CO_2$ in said drainage canister.

19. The device of claim 1, further comprising a manipulation device effective to deliver energy or motion to the clearance member.

20. A method of clearing obstructions from a medical tube, comprising establishing fluid communication between said medical tube and an interior of a drainage canister for collecting material drained through said medical tube, drawing a suction through said medical tube and through said drainage canister in fluid communication therewith, and advancing a guide member that extends from said canister through said medical tube, said guide member being biased adjacent a proximal end thereof in a normally-inserted position wherein the guide member is advanced to a maximum extent through said drainage port.

21. The method of claim 20, further comprising inserting a distal end of said medical tube inside the body of a patient.

22. The method of claim 20, further comprising providing a drainage tube intermediate and in fluid communication with said medical tube and said drainage canister, said guide member being advanced through both said drainage tube and said medical tube.

23. The method of claim 20, further comprising operating a guide-member actuator to reversibly advance or withdraw a clearance member disposed or attached in a distal region of said guide member through said medical tube.

24. The method of claim 23, said medical tube being a chest tube.

25. A medical tube drainage system comprising:
a drainage canister having a fluid chamber;
a drainage tube having a proximal end and a distal end, the proximal end being coupled to the drainage canister via a drainage port thereof, the drainage tube comprising a lumen therethrough, the drainage tube lumen being in fluid communication with the fluid chamber;
a medical tube having a proximal end and a distal end, the medical tube comprising a lumen therethrough, the proximal end of the medical tube being coupled to the distal end of the drainage tube, the medical-tube lumen being in fluid communication with the lumen of the drainage tube; and
a guide wire having a proximal portion terminating at a proximate end and a distal portion terminating at a distal end, the proximal portion of the guide wire extending through the fluid chamber and at least partially out of said drainage canister through an actuator port, the distal portion of the guide wire extending through the lumen of the drainage tube and into the lumen of the medical tube, wherein the guide wire is adapted such that the distal end of the guide wire can be extended into and withdrawn from the medical tube by pushing and pulling the guide wire proximal end, the distal end of the guide wire being adapted to dislodge obstructing material from the medical tube, the proximal portion of the guide wire being biased so that said proximal portion is in either a normally-inserted position wherein the guide wire is advanced to a maximum extent into said drainage canister through said actuator port, or a normally-withdrawn position wherein said proximal portion is withdrawn to a maximum extent from said canister through said actuator port.

26. A medical tube drainage system comprising:

a drainage canister having a fluid chamber;

a drainage tube having a proximal end and a distal end, the proximal end being coupled to the drainage canister via a drainage port thereof, the drainage tube comprising a lumen therethrough, the drainage tube lumen being in fluid communication with the fluid chamber;

a medical tube having a proximal end and a distal end, the medical tube comprising a lumen therethrough, the proximal end of the medical tube being coupled to the distal end of the drainage tube, the medical-tube lumen being in fluid communication with the lumen of the drainage tube;

a guide wire having a proximal portion terminating at a proximate end and a distal portion terminating at a distal end, the proximal portion of the guide wire extending through the fluid chamber and at least partially out of said drainage canister through an actuator port, the distal portion of the guide wire extending through the lumen of the drainage tube and into the lumen of the medical tube, wherein the guide wire is adapted such that the distal end of the guide wire can be extended into and withdrawn from the medical tube by pushing and pulling the guide wire proximal end, the distal end of the guide wire being adapted to dislodge obstructing material from the medical tube; and a sheath coupled to the drainage canister and the proximal end of the guide wire, the sheath adapted to contain that portion of the guide wire proximal portion that extends from the drainage canister through the actuator port, the sheath being flexible so as to allow expansion and contraction thereof as the guide wire proximal portion is withdrawn from and inserted into the drainage canister, respectively, through said actuator port.

27. The system of claim 26 further comprising means for guiding the proximal portion through the drainage canister.

28. The system of claim 25, said proximal portion being biased in said normally-inserted portion such that the distal end of said guide wire rests within the medical tube adjacent a distal end of said medical tube when the guide wire is not engaged by a user.

29. The system of claim 25, wherein the guide wire comprises a loop at the guide wire distal end, the loop extending in a plane that is at a predetermined angle from the guide wire, the loop defining an aperture adapted to allow the passing of material therethrough, the loop adapted to contact at least a portion of an interior wall of the medical tube lumen.

30. The debris-removal system of claim 25, wherein the guide wire comprises a guide lumen adapted to transport fluid from a port in fluid communication with a proximal end of said guide lumen and to expel said fluid through openings in fluid communication with a distal end of said guide lumen.

31. The debris-removal system of claim 30, wherein the fluid is selected from the list consisting of anticoagulant, antineoplastics, thrombolytics, antibiotics, pleurodesis agents, and pain medication.

32. The debris-removal system of claim 30, wherein the guide lumen is adapted to communicate a vacuum from said port and provide a vacuum at said openings in communication with the distal end of said guide lumen.

33. The device of claim 7, said guide member being attached to said handle portion at a proximal end of said guide member.

* * * * *